(12) United States Patent
Baron

(10) Patent No.: US 10,460,706 B2
(45) Date of Patent: Oct. 29, 2019

(54) INTEGRATED REED PROTECTION AND STORAGE METHODS AND SYSTEMS

(71) Applicant: Musically Overjoyed, LLC, Tampa, FL (US)

(72) Inventor: James Baron, Tampa, FL (US)

(73) Assignee: MUSICALLY OVERJOYED, LLC, Tampa, FL (US)

( * ) Notice: Subject to any disclaimer, the term of this patent is extended or adjusted under 35 U.S.C. 154(b) by 0 days.

(21) Appl. No.: 16/020,173

(22) Filed: Jun. 27, 2018

(65) Prior Publication Data

US 2019/0108819 A1    Apr. 11, 2019

Related U.S. Application Data

(60) Provisional application No. 62/570,954, filed on Oct. 11, 2017.

(51) Int. Cl.
| | | |
|---|---|---|
| *G10D 9/02* | (2006.01) | |
| *A61L 2/18* | (2006.01) | |
| *B27K 9/00* | (2006.01) | |
| *A61L 2/26* | (2006.01) | |

(52) U.S. Cl.
CPC .............. *G10D 9/023* (2013.01); *A61L 2/18* (2013.01); *A61L 2/26* (2013.01); *B27K 9/005* (2013.01); *B27K 2240/20* (2013.01)

(58) Field of Classification Search
CPC .......... G10D 9/023; G10G 7/00; A61L 2/235; A61L 2/18; A61L 2/26; B27K 9/005; B27K 2240/20
See application file for complete search history.

(56) References Cited

U.S. PATENT DOCUMENTS

| | | |
|---|---|---|
| 4,250,995 A | 2/1981 | Lorenzini |
| 4,674,630 A | 6/1987 | Kirck |
| 5,221,004 A | 6/1993 | Murphy |
| 5,379,673 A * | 1/1995 | Vogt ...................... G10D 9/023 424/53 |

OTHER PUBLICATIONS http://reedjuvinate.com/, Copyright 2017 reedjuviate.com.

* cited by examiner

*Primary Examiner* — Kimberly R Lockett
(74) *Attorney, Agent, or Firm* — Stanton IP Law Firm, P.A.

(57) ABSTRACT

An integrated reed protection and storage system is provided. The system includes a controlled solution container. The system also includes a sponge material positionable within the container. Further, the system includes at least one reed holder positionable around the sponge material. Additionally, the system includes at least one reed, the at least one reed positionable on the at least one reed holder. The at least one reed is configured to contact a surface of the sponge material.

8 Claims, 3 Drawing Sheets

INTEGRATED REED PROTECTION AND STORAGE METHODS AND SYSTEMS

CROSS-REFERENCE TO RELATED APPLICATIONS

This application claims priority to provisional application 62/570,954 filed on Oct. 11, 2017, and is incorporated herein, by reference in its entirety.

FIELD OF THE INVENTION

The present invention relates generally to reeds, and more particularly, to integrated reed protection and storage methods and systems, which utilize a spray bottle, solution, sponge material, and a controlled solution container, operating in concert, to soak, wet, protect, maintain, and repair, reeds.

BACKGROUND OF THE INVENTION

Many methods and systems have been used attempting to maintain reeds functional and operational for longer periods of time. Several devices and methods have been created attempting unsuccessfully to solve the problem of reed damage and reduced reed life span due to environmental conditions. These previous systems and methods have not been effective in solving the problem of shortened reed life spans.

Musicians presume that reeds will deteriorate over time and that the reeds will no longer function properly after a short period of time. Most reed user experiences indicate that reeds will have a relatively short life span. Many musicians accept that reeds will have to be replaced often. This occupational reality is prevalent amongst those who use reeds.

A reed is a strip of material which vibrates to produce a sound on an instrument. Reeds of woodwind instruments may consist of organic or synthetic material. Woodwind instruments such as saxophones, clarinets, bassoons, and oboes use reeds. Reeds used on many of these woodwind instruments can be affected by the environment in which they are kept. Temperature and humidity conditions of the reed's environment can change the reed's physical and operating characteristics. A reed may behave differently in different environments.

Past attempts to reduce reed damage due to environmental conditions have included drying and moistening reeds cyclically. Previous methods and systems also included charcoal desiccants. However, these processes cause cracking and other damage to the reeds due to the process of swelling and shrinkage of the reed material. Additionally, these processes allow the formation of mold on the reeds causing further damage to the reeds. Previous methods attempted unsuccessfully to mitigate mold growth on reeds.

Reeds include a tip on one end and a heel on an opposite end, with a profile interposed between. The condition and thickness of the tip, heel, and the profile in between can affect the acoustical characteristics of the sound produced by the instrument. Previous methods and systems used to protect and extend reed life spans did not adequately treat the reeds for profile dissimilarities.

Accordingly, there is an established need for integrated reed protection and storage methods and systems which solve at least one of the aforementioned problems. Further, there is an established need for integrated reed protection and storage methods and systems which can reduce costs, increase reed life span, resist mold growth, provide a sturdy storage container, and may be used for any woodwind reed.

SUMMARY OF THE INVENTION

The present invention is directed to effective, convenient and cost-saving integrated reed protection and storage methods and systems. These methods and systems are used to increase reed operating life spans, provide a solution controlled environment for reeds that is antimicrobial and non-toxic, and that maintains a moisture level in stored reeds similar to moisture levels in reeds while in use.

In an aspect of the present invention, an integrated reed protection and storage system is provided. The system includes a controlled solution container. The system also includes a sponge material positionable within the container. Further, the system includes at least one reed holder positionable around the sponge material. Additionally, the system includes at least one reed, the at least one reed positionable on the at least one reed holder. The at least one reed is configured to contact a surface of the sponge material.

In another aspect of the present invention, a method for preparing a reed for use is provided. The method includes soaking at least one reed in a solution. The method also includes removing the at least one reed from the solution. Additionally, the method includes storing the at least one reed in a controlled solution container.

In yet another aspect a method for preserving a reed after use is provided. The method includes wetting at least one reed with a solution. The method also includes storing the at least one reed in a controlled solution container.

These and other objects, features, and advantages of the present invention will become more apparent from the attached drawings and the detailed description of the preferred embodiments, which follow. It is understood, that the drawings are designed for the purposes of illustration and not as a definition of the limits of the embodiments of the present invention. It should be further understood that the drawings are not necessarily drawn to scale and are merely intended to conceptually illustrate the methods and systems described herein.

BRIEF DESCRIPTION OF THE DRAWINGS

The preferred embodiments of the invention will hereinafter be described in conjunction with the appended drawings provided to illustrate and not to limit the invention, where like designations denote like elements, and in which.

Like reference numerals refer to like parts throughout the several views of the drawings.

DETAILED DESCRIPTION

The following detailed description is exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Shown throughout the figures, embodiments of the present invention are directed towards methods and systems for protecting and storing reeds for increasing life span and minimizing damage to the reeds.

Figure 1:
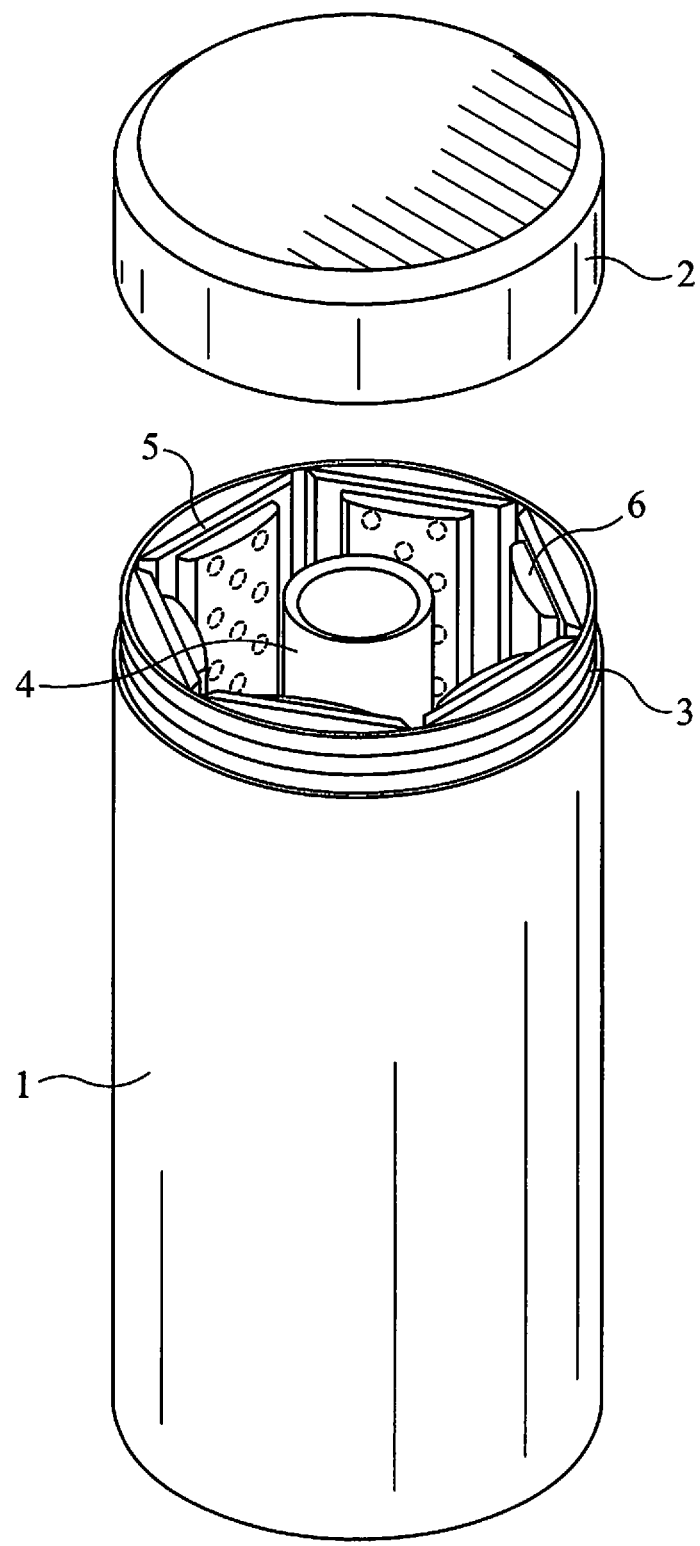
FIG. 1 presents a perspective view of an integrated reed protection and storage system with a sealable cap, in accordance with an embodiment of the present invention.

Referring initially to FIG. 1, an integrated reed protection and storage system is illustrated with an embodiment of the present invention. The integrated reed protection and storage system can include a controlled solution container 1. As seen in the present embodiment, a sealable cap 2 can include mating threads, not shown, to mate with container 1. As displayed, the solution controlled container 1 can include threads 3 on a top open side of the container 1. The threads 3 of the container 1 mate with the threads of the sealable cap 2. Positionable within the container 1 is a spray bottle 4. The spray bottle 4 can be configured with, not shown, various types of spray tops including, but not limited to, finger pumps, spray misters, hand pumps, and/or any commercially obtained spray bottle type which may allow solution to spray out of the spray bottle 4, onto reed holders 5, reeds 6, within the container 1, directly onto a sponge material 7, as shown in FIGS. 2 and 4, and/or as necessary to soak or wet the reeds 6 or to saturate the container 1 in accordance with embodiments of the present invention.

Figure 2:
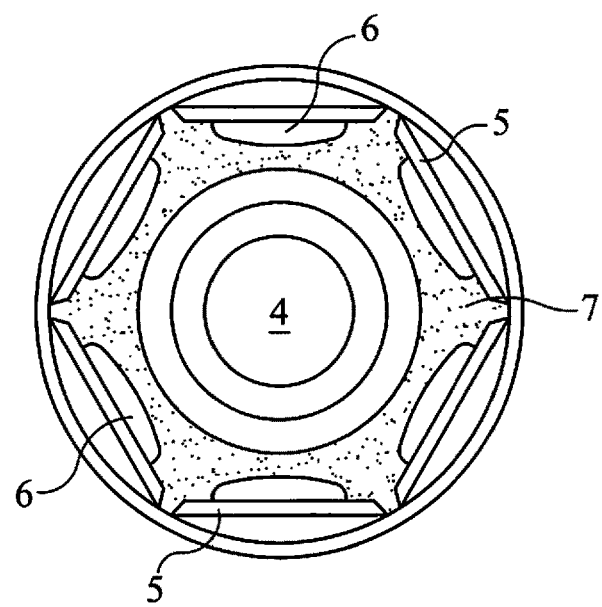
FIG. 2 presents a top view of the integrated reed protection and storage system showing components inside a controlled solution container.
Figure 4:
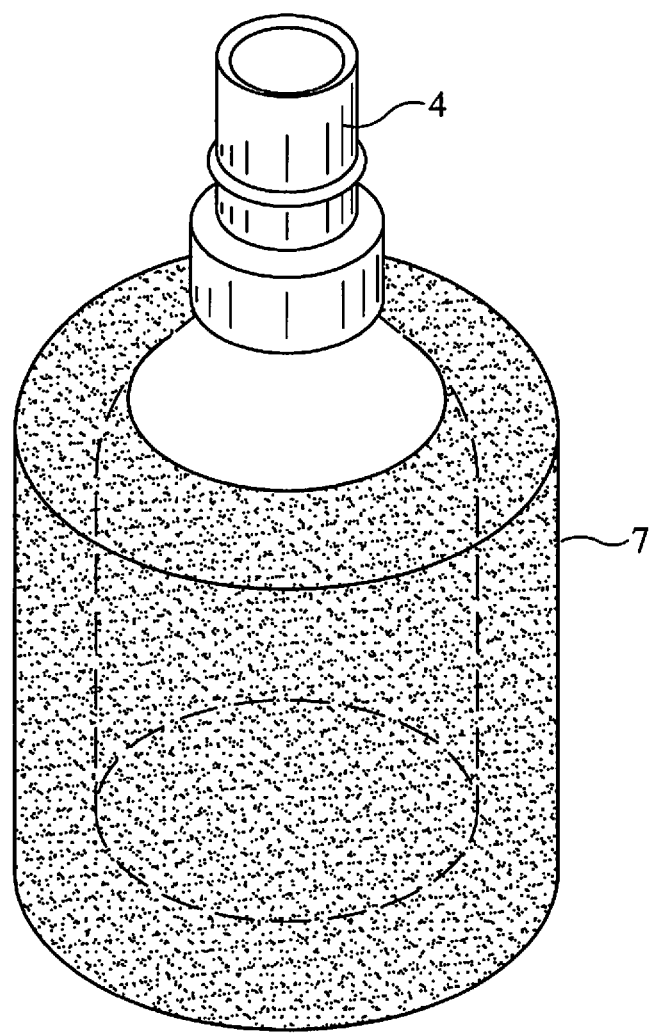
FIG. 4 presents a perspective view of a sponge material around a spray bottle, in accordance with an embodiment of the present invention.

Continuing with FIG. 1, the reed holders 5 are positionable around the spray bottle 4 and around the sponge material 7, as seen in FIGS. 2 and 4. The reeds 6 can be positionable on the reed holders 5 and can be configured to contact a surface of the sponge material 7, as displayed in FIG. 2. As shown in FIG. 2, reed holders 5 can contain holes 8. A solution, not shown, can be placed within the spray bottle 4. The solution may be capable of being placed within the spray bottle 4 and/or the container 1. The solution can include, but is not limited to, antiseptic, antimicrobial, a non-toxic component, water, solvent, mouthwash, disinfectant, germicidal, antibiotic, anti-fungal, and/or anti-viral components. In an embodiment, the solution includes an aqueous composition including water and a non-toxic antimicrobial. The solution can be designed for different thicknesses of reeds, different reed materials, and different target reed moisture levels. The solution can be sprayed from the spray bottle 4 and/or wetted and/or applied directly to the reeds 6 and/or directly to the sponge material 7.

As best shown in FIG. 2, the spray bottle 4 is positionable within the container 1. The sponge material 7 is positionable around the spray bottle 4. The reed holders 5 are positionable around the sponge material 7. The reeds 6 are positionable on the reed holders 5 and the reeds 6 are configured to contact a surface of the sponge material 7. The spray bottle 4 can be removed from the container 1 without damaging the sponge material 7.

Figure 3:
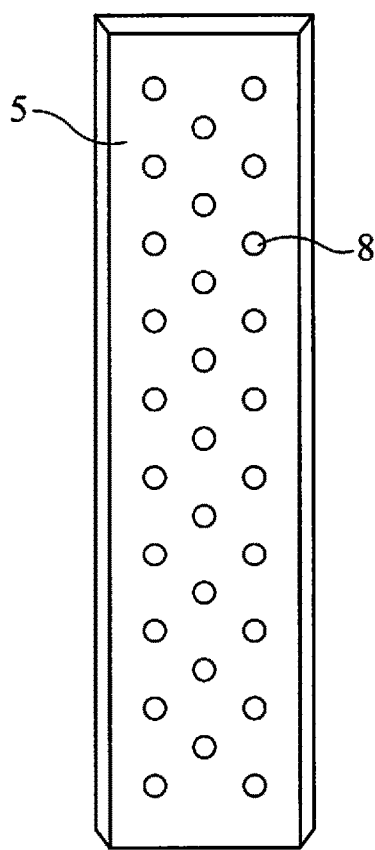
FIG. 3 presents a side view of a reed holder.

Next, as illustrated in FIG. 3, reed holders 5 in an embodiment of the invention are shown. The reed holders 5 can include holes 8. The holes 8 pass entirely through the reed holders 5, such that a flat surface for holding the reeds 6 is in fluid communication with an opposite side of the reed holder 5. Solution, not shown, may pass through the holes 8 of the reed holders 5 and may return to the bottom of the container 1.

In an embodiment as shown in greater detail in FIGS. 2 and 4, the sponge material 7 can be of annular shape fitted around the spray bottle 4, such that the spray bottle 4 may be centered in the container 1. The sponge material 7 can maintain the reeds 6 moistened with the solution. The reeds 6 are positionable on the reed holders 5 and are configured to contact a surface of the sponge material 7.

A controlled solution container 1 may include, but is not limited to, hygrostats, humidity controls, temperature controls, liquid level controls, sponge material controls, controlled solution controls, temperature controls, and sensors to indicate humidity and/or temperature and/or controlled solution level.

The sponge material 7 may include, but is not limited to, an organic and/or synthetic sponge, organic and/or synthetic material, and/or hygrostat material. The sponge material 7 characteristics can be designed to vary controlled solution absorption rate and/or controlled solution diffusion rate into and out of the reeds 6 in contact with the sponge material 7. The sponge materials 7 may be designed to vary absorption and/or diffusion rate based on but not limited to, for example, material composition of the reeds 6, the number of reeds, thickness of the reeds 6, type of instrument the reed will be utilized with, sponge material chosen, and altitude and environmental conditions where the reeds 6 will be used. Further, the sponge materials 7 may be designed for wicking solution onto and off the reeds 6. Additionally, the sponge materials 7 may be designed to maintain specific humidity within the controlled solution container 1 ambient environment.

In an embodiment of an integrated reed protection and storage method, the reeds 6 can be soaked in the solution prior to use. The reeds 6 can be immersed in the solution and/or saturated with the solution. Prior to use, the reeds 6 of different styles and thicknesses may require different soaking times in order to saturate the reeds 6. In an embodiment of a method of preparing the reeds 6 for use, soaking time of the reeds 6 in the solution may be around 24 hours. In embodiments, soaking of the reeds 6 may be by full immersion of the reeds 6 within the solution. In embodiments, soaking of the reeds 6 can by performed by direct application of the solution, direct spraying of the solution, or by direct continuous contact with the sponge material 7 for a specified soak time. Soak time can be, for example, 12 hours, 24 hours, and/or 36 hours.

In an embodiment of an integrated reed protection and storage method, the reeds 6 can be wetted with the solution after use. During use, the reeds 6 are in the mouths of musicians. After use, the reeds 6 can be wetted with solution. Wetting the reeds 6 with solution can prepare the reeds 6 for storage in the controlled solution container 1. Wetting the reeds 6 after use can be performed by full immersion of the reeds 6 within the solution, direct application of the solution, spraying solution directly on the reeds 6, and/or by direct contact of the reeds 6 with the sponge material 7. In embodiments, wetting of the reeds 6 can be performed by wetting both sides of the reeds 6 prior to storage in the controlled solution container 1. In embodiments, wetting of the reeds 6 includes wetting opposing surfaces of the reeds 6. In embodiments, the reeds 6 remain in substantial contact with a substantial portion of a surface of the sponge material 7 while being stored in the container 1. In embodiments, an entire surface of the reeds 6 remains in full contact with a surface of the sponge material 7 while being stored in the container 1.

The reeds 6 may include organic and/or synthetic material. The reeds 6 may include cane reeds.

In some embodiments, the integrated reed protection and storage systems methods and systems minimize drying out of the reeds 6. In some embodiments the integrated reed protection and storage systems mitigate drying out of the reeds 6 during periods of non-use with wetting of the reeds 6 after use and/or storing the reeds after wetting in a controlled solution container 1.

In an embodiment of the present invention, a reed case and hygrostat for wind wood reeds includes an air tight housing, a spray bottle 4 containing a non-toxic antimicrobial solution, a hygrostat material surrounding the spray bottle 4, reed holders 5 disposed around the hygrostat material, such that reeds 6 held flat against the reed holders 5 contact the surface of the hygrostat material when stored, and the housing surrounding and keeping the reed holders 5 and the reeds 6 in position within the housing.

In an embodiment of the present invention, a resealable cap 2, such as a cap threadingly engaging the housing, can be used to seal the housing. In embodiments, a resealable top, such as a locking O-ring top clamped onto the container 1 may be used.

In an embodiment of the present invention, a wood wind reed hygrostat may include a housing, closed at one end and having a sealable lid on an opposite end. A plurality of reed holders 5, each having a flat surface for supporting a reed and holes 8 extending through the flat surface to an opposite surface of the holder, such that air and moisture flow freely through the holes 8, are provided for holding reeds 6. A hygrostat material, such as a sponge, may be disposed annularly about a spray bottle 4 containing an antibacterial spray. The spray bottle 4 may be removed from the hygrostat material, without damaging the hygrostat material, for example. The spray bottle 4 may be used with or without the hygrostat material remaining on the spray bottle 4. The spray bottle 4 may contain an antibacterial spray, such as a solution comprised of a mouthwash composition.

In other embodiments, not shown, the integrated reed protection and storage methods and systems can be used by commercial musician groups who would use containers 1 of various sizes to handle various sizes of reeds 6. In embodiments not shown, the containers 1 may or may not contain spray bottles 4. In embodiments not shown, the various sizes of the containers 1 may be configured to be positionable within a shirt pocket and/or a pant pocket and/or a handbag.

In embodiments not shown, shapes of the containers 1 may be, but not limited to, rectangular, oval, oblong, cylindrical, and/or shaped to carry and/or fit in a person's hand. In embodiments not shown, the containers 1 may be configured to contain a reed 6.

In embodiments not shown, combinations of the spray bottle 4, the sponge material 7, the reeds 6, the reed holders, the container 1, the threads 3, the holes 8, and/or the cap 2, may be included or excluded in the embodiments. Further, in embodiments not shown, the spray bottle 4, the sponge material 7, the reeds 6, the reed holders, the container 1, the threads 3, the holes 8, and/or the cap 2, may be positioned and/or configured in any interchangeable manner.

Since many modifications, variations, and changes in detail can be made to the described preferred embodiments of the invention, it is intended that all matters in the foregoing description and shown in the accompanying drawings be interpreted as illustrative and not in a limiting sense. Furthermore, it is understood that any of the features presented in the embodiments may be integrated into any of the other embodiments unless explicitly stated otherwise. The scope of the invention should be determined by the appended claims and their legal equivalents.

What is claimed is:

1. An integrated reed protection and storage system comprising:
   a controlled solution container;
   a sponge material positionable within the container;
   at least one reed holder positionable around the sponge material; and
   at least one reed, the at least one reed positionable on the at least one reed holder wherein the at least one reed is configured to contact a surface of the sponge material.

2. The system as recited in claim 1, further comprising a spray bottle positionable within the container.

3. The system as recited in claim 2, further comprising a solution, the solution capable of being placed within the spray bottle and/or the container, wherein the solution includes water and a non-toxic anti-microbial.

4. The system as recited in claim 2, wherein the sponge material is positionable around the spray bottle.

5. The system as recited in claim 1, wherein the controlled solution container includes a cylindrical housing, the cylindrical housing closed on one end and/or having a sealable lid on an opposite end.

6. The system as recited in claim 1, wherein the at least one reed holder includes through holes passing entirely through the at least one reed holder configured such that air and/or liquid and/or solution can flow freely through the holes.

7. The system as recited in claim 1, wherein the surface of the sponge material is configured to contact a substantial portion of a surface of the at least one reed.

8. The system as recited in claim 1, wherein the controlled solution container includes a hygrostat.

\* \* \* \* \*